United States Patent [19]

Bellinger

[11] Patent Number: 5,119,682
[45] Date of Patent: Jun. 9, 1992

[54] FACE LEVEL SAMPLING DEVICE

[75] Inventor: Edward G. Bellinger, Bolton, England

[73] Assignee: The Victoria University of Manchester, Manchester, England

[21] Appl. No.: 548,969

[22] PCT Filed: Feb. 1, 1989

[86] PCT No.: PCT/GB89/00022
§ 371 Date: Aug. 1, 1990
§ 102(e) Date: Aug. 1, 1990

[87] PCT Pub. No.: WO89/07250
PCT Pub. Date: Aug. 10, 1989

[30] Foreign Application Priority Data

Feb. 5, 1988 [GB] United Kingdom ............... 8802699

[51] Int. Cl.⁵ .................................. G01N 1/24
[52] U.S. Cl. ..................... 73/864.73; 73/863.03; 73/863.25; 73/863.33; 73/864.34
[58] Field of Search ............... 128/730; 73/864.73, 73/23.3, 864.34, 864.35, 863.02, 863.03, 863.23, 863.24, 863.25, 864.74, 863.33

[56] References Cited

U.S. PATENT DOCUMENTS

| | | | |
|---|---|---|---|
| 3,956,940 | 5/1976 | Guild | 73/863.23 |
| 4,080,832 | 3/1978 | Moody et al. | 73/863.23 |
| 4,589,292 | 5/1986 | Delhaye et al. | 73/863.03 |
| 4,721,517 | 1/1988 | Cloutier | 73/863.23 X |
| 4,858,476 | 8/1989 | Tobin | 73/863.23 |
| 4,961,916 | 10/1990 | Lesage et al. | 73/863.23 X |

FOREIGN PATENT DOCUMENTS

| | | | |
|---|---|---|---|
| 1083058 | 9/1967 | United Kingdom | 73/23.3 |
| 1180300 | 2/1970 | United Kingdom | 73/864.73 |
| 1401898 | 8/1975 | United Kingdom | . |
| 2046439 | 11/1980 | United Kingdom | 73/863.03 |
| 2048468 | 12/1980 | United Kingdom | . |
| 2205158 | 11/1988 | United Kingdom | 73/864.73 |

Primary Examiner—Tom Noland
Attorney, Agent, or Firm—Nies, Kurz, Bergert & Tamburro

[57] ABSTRACT

A face level sampling device comprising a headband (10) carrying a suction pump (11) and power pack (13). Connected to pump (11) is a rigid or semi-rigid tubular stalk (12) having a sample head at its free end which is thus positioned in the immediate vicinity of the wearer's nose and mouth in order to take a sample of the environmental contents in the immediate breathing zone.

12 Claims, 2 Drawing Sheets

FACE LEVEL SAMPLING DEVICE

BACKGROUND OF THE INVENTION

This invention concerns personal samplers for detecting the presence of hazardous materials in a working environment, in order to ensure occupational hygiene and safety.

Stringent environmental control in the working environment is imposed to ensure that hazardous materials or conditions such as poisonous gases, micro-organisms or radioactivity, can be detected without delay. Devices to detect such hazards, known as personal samplers, usually consist of a sampling head fixed to the lapel of the user and connected by flexible tubing to a pump and battery pack carried on the back or on a belt at the waist.

These devices are cumbersome to the wearer, expensive to produce and often produce a false reading of the environmental contents at chest level which may be different from those collected in the immediately adjacent breathing zone around the nose and mouth.

An object of the present invention is to provide a personal sampler which is considerably more compact and less expensive to produce and is designed to sample the atmospheric contents as near as possible to the nose and mouth.

SUMMARY OF THE INVENTION

According to the present invention there is provided a face level sampling device comprising a suction pump, a power pack electrically connection to the suction pump, a sample head connected to the suction pump by a reformable and non-flexible tubular stalk, and means for supporting at least the suction pump and stalk on the wearer's head such that the sample head is disposed in use close to the wearer's nose and mouth thus to sample the atmospheric conditions within the breathing zone.

BRIEF DESCRIPTION OF THE DRAWINGS

An embodiment of the invention will now be described, by way of example only, with reference to the accompanying drawings in which.

DESCRIPTION OF THE PREFERRED EMBODIMENTS

Figure 1:
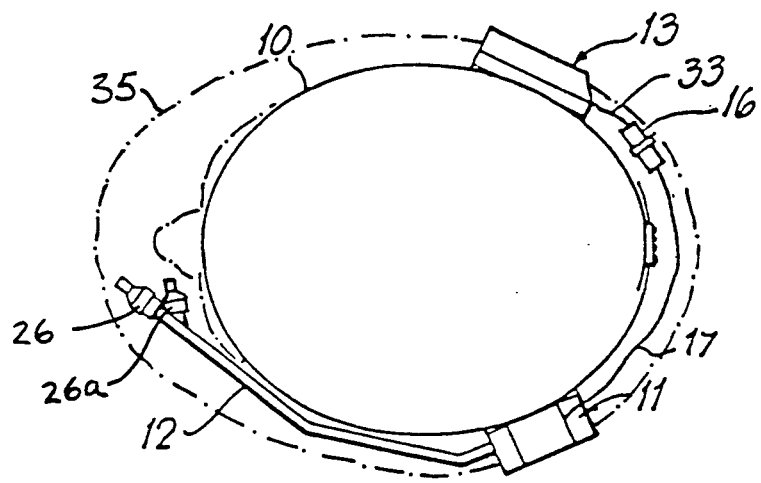
FIG. 1 is a plan view of a face level sampling device as worn.

Referring now to the drawings, the sampling device comprises an adjustable headband 10 worn at forehead level and carrying a small suction pump 11 from which extends a rigid of semi-rigid tubular stalk 12 which is configured to extend past the cheek to the breathing zone immediately adjacent the wearer's nose and mouth.

Electrically connected to the suction pump is a power pack 13 to be described in further detail and adapted to drive the pump 11.

Figure 2:
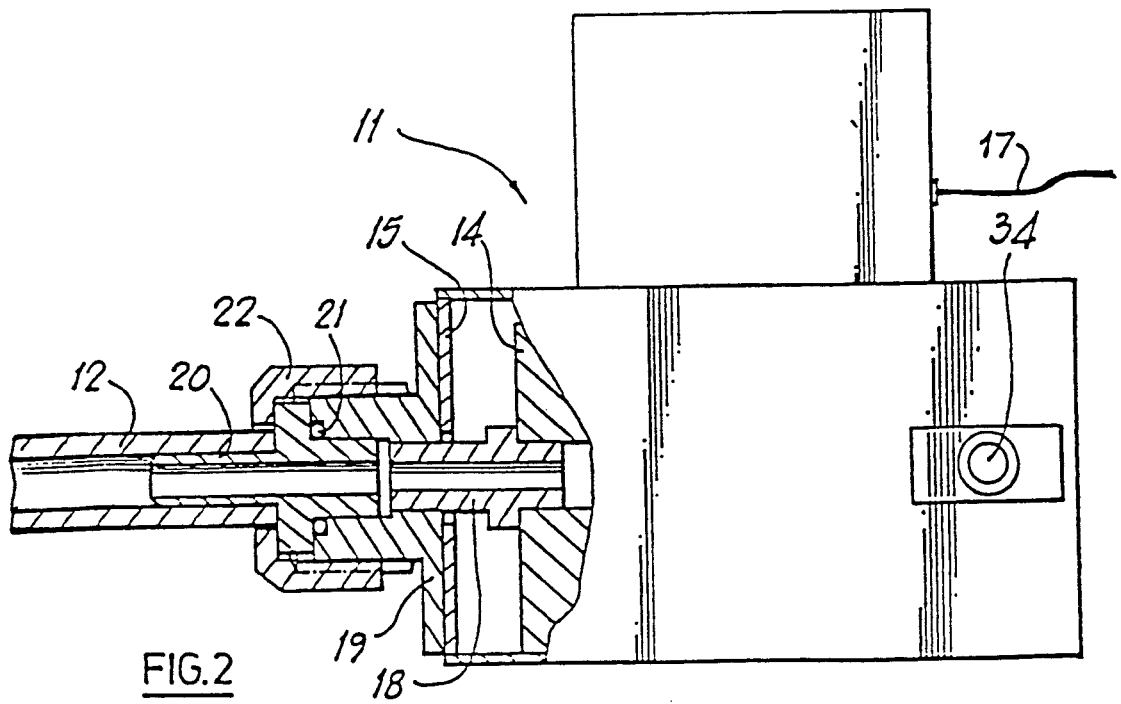
FIG. 2 is a partly cross-sectional side view of a suction pump to be supported on a headband and forming part of the device.

As can be seen in FIG. 2 the pump 11 in further detail consists of a motor driven impeller or fan 14 mounted in a casing 15. An electrical connector 16 (See FIGS. 1 and 4) and lead 17 supplies power from the power pack 13 to drive the pump. An inlet tube 18 for the pump is connected to a body 19 which receives a plug 20 with the interposition of a sealing ring 21. The plug 20 is held in place by a locking ring 22 and receives, coaxially as a push fit, one end of the stalk 12.

The stalk 12 is of a reformable material such as polycarbonate which can be heated and then configured or tailored to suit a particular wearer so that the free end of the stalk which carries the sample head will be positioned as close as possible to the immediate breathing zone of the wearer. This accurate location is further enhanced by the ability to rotate the plug 20 and stalk 12 after releasing locking ring 22 thus slightly to raise or lower the sampling head to bring it as close as possible to the nose and mouth.

Figure 3:
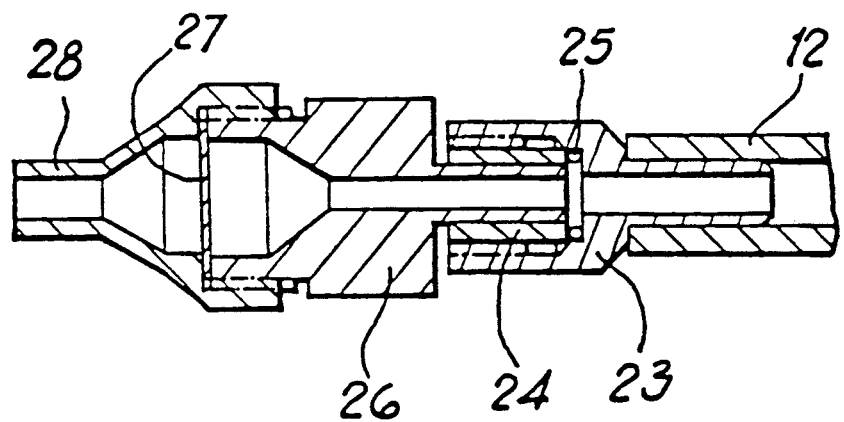
FIG. 3 is a part sectional side view of a sampling head forming part of the device.

Referring now to FIG. 3, the free end of the stalk 12 carries the sampling head which consists of a head carrier 23 into which is screwed an adaptor 24 with the interposition of a sealing ring 25. The adaptor receives as a resistance fit a sampling head 26 having a central bore coaxial with that of carrier 23 and stalk 12. The other end of head 26 where the central bore is enlarged, has removably held thereto a sheet 27 of filter medium which is removably retained by a cap 28 screwed onto head 26.

Figure 4:
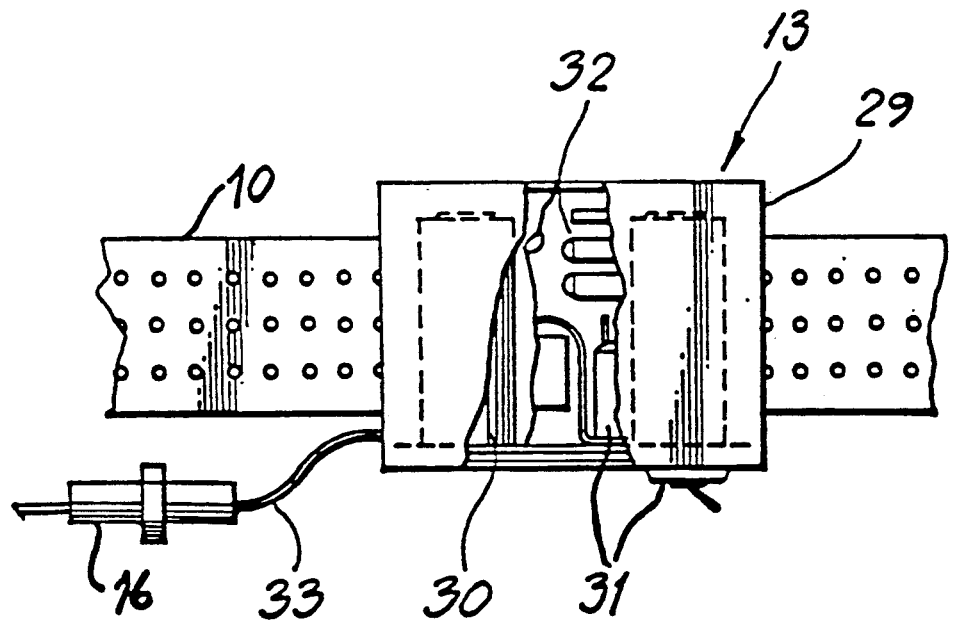
FIG. 4 is a partially cut away side view of a power pack also forming part of the device.

Referring now to FIG. 4, the power pack 13 consists of a casing 29 housing one or more rechargeable batteries 30. The power pack also includes an on/off switch 31 and a constant current/voltage control circuit, some of the components of which are illustrated at 32. A lead 33 connects the power pack to connector 16. For convenience, recharging of batteries 30 may be effected by connecting the proximal half of connector 16 to a conventional battery charger.

In use, by operating on/off switch 31, pump 14 is energised to draw air through the sampling head and thus across the filter medium 27. If required, the flow of air may be regulated by a throttle valve 34 associated with pump 14.

The pump may be operated intermittently or continuously during a working period and, at predetermined intervals, the filter medium 27 is replaced and the sheet removed is taken for analysis. The filter medium may be one of various types capable of sampling the dust content of the atmosphere or the presence of noxious gases or vapours. Again it may be in the form of a bacteriological filter for microbial evaluation, or a radioactivity sensor. The medium may respond to adverse conditions by a change in or other visual physical property.

It is intended that the entire device or parts thereof should be designed to be accommodated within other working head gear such as a protective helmet, as illustrated schematically at 35 in FIG. 1, whilst the proximity of the sampling head to the nose and mouth enables it to be enclosed within or behind a face mask which may form part of such head gear. In another form of the device, as shown in FIG. 1, there may be two or more tubular stalks and sampling heads 26, 26a connected alternatively or simultaneously to the suction pump 11 thus, for example, to sample different environmental contents simultaneously. In such an arrangement the sample heads and/or their connecting stalks may be individually identified or colour coded for ease of analysis and recordal.

When compared with conventional lapel mounted samplers the present device provides several advantages, being simple and inexpensive in construction, and smaller and lighter than the conventional devices and thus more acceptable to the wearer. Also, the suction pump is almost silent in operation. All of these advantages encourage the wearer to use the device in a proper manner thus discouraging cheating.

The current/voltage control circuit ensures constant air flow through the sample head as the filter medium becomes contaminated. The rate of flow is maintained within ±10% of that required to produce a correct sample.

I claim:

1. A face level sampling device comprising a sample head connected by a reformable and non-flexible tubular stalk to a suction pump, a power pack electrically connected to the pump, and means for supporting at least the sample head so as to be disposed in use close to the wearer's nose and mouth thus to sample the atmospheric contents within an immediately adjacent breathing zone of the wearer.

2. A face level sampling device according to claim 1, wherein the suction pump and the power pack are mounted at spaced positions on an adjustable headband to be worn generally at forehead level, the tubular stalk extending from the suction pump to a position immediately adjacent the nose and mouth.

3. A face level sampling device according to claim 1, wherein the sample head contains a removable sheet of filter medium across which air from the wearer's breathing zone is drawn by the suction pump.

4. A face level sampling device according to claim 1, including means for adjusting the position of the sample head with respect to that of the suction pump.

5. A face level sampling device according to claim 1 wherein said power pack contains a constant current circuit to ensure a constant air flow through the sample head.

6. A face level sampling device according to claim 1 wherein said power pack contains rechargeable batteries and carries an on/off switch for use by the wearer.

7. A face level sampling device according to claim 1, wherein the tubular stalk is produced from polycarbonate.

8. A face level sampling device according to claim 1, including two or more sample heads.

9. A face level sampling device according to claim 1, including means for adjustment of the air flow through the sample head.

10. A face level sampling device according to claim 1, wherein at least a part of the device is attached to other working head gear.

11. A face level sampling device according to claim 1, including an electrical connector between the suction pump and the power pack which when separated may be connected to a battery charger to recharge the batteries in the power pack.

12. A face level sampling device according to claim 1, wherein said power pack contains a constant voltage circuit to ensure a constant air flow through the sample head.

* * * * *